United States Patent [19]

Clausen et al.

[11] Patent Number: 5,061,289
[45] Date of Patent: Oct. 29, 1991

[54] OXIDATION HAIR DYE COMPOSITION CONTAININNG DIAMINOPYRAZOL DERIVATIVES AND NEW DIAMINOPYRAZOL DERIVATIVES

[75] Inventors: Thomas Clausen, Alsbach; Ute Kern, Darmstadt-Arheilgen; Hans Neunhoeffer, Mühltal, all of Fed. Rep. of Germany

[73] Assignee: Wella Aktiengesellschaft, Darmstadt, Fed. Rep. of Germany

[21] Appl. No.: 573,173

[22] PCT Filed: Nov. 30, 1989

[86] PCT No.: PCT/EP89/01449
§ 371 Date: Aug. 2, 1990
§ 102(e) Date: Aug. 2, 1990

[87] PCT Pub. No.: WO90/07504
PCT Pub. Date: Jul. 12, 1990

[30] Foreign Application Priority Data

Dec. 24, 1988 [DE] Fed. Rep. of Germany ....... 3843892

[51] Int. Cl.$^5$ .................. A61K 7/13; C07C 211/00
[52] U.S. Cl. ........................... 8/405; 8/406; 8/414; 8/415; 8/416; 8/421; 8/425; 8/428; 8/429; 564/442
[58] Field of Search .................. 8/405, 406, 414, 415, 8/416, 421, 425, 428, 429; 564/442

[56] References Cited

FOREIGN PATENT DOCUMENTS 2160317 6/1973 Fed. Rep. of Germany .
2160318 6/1973 Fed. Rep. of Germany .

Primary Examiner—Paul Lieberman
Assistant Examiner—William S. Parks
Attorney, Agent, or Firm—Michael J. Striker

[57] ABSTRACT

Composition for the oxidative dyeing of hair based on a combination of developer substances and coupler substances contains, as developer substance, a diaminopyrazol of the general formula (I),

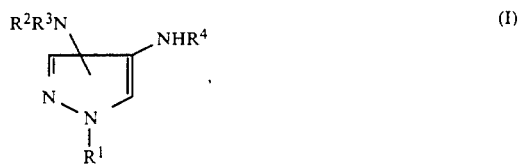

wherein $R^1$, $R^2$ and $R^4$ are identical or different and designate hydrogen, alkyl with 1 to 4 carbon atoms, hydroxyalkyl with 2 to 4 carbon atoms, benzyl or phenyl, and $R^3$ is hydrogen, alkyl with 1 to 4 carbon atoms, hydroxyalkyl with 2 to 4 carbon atoms, with the proviso that the amino groups are in 3,4 or 4,5 position, or its physiologically tolerated, water-soluble salt, new diaminopyrazol derivatives of the above general formula I are also described herein in which $R^1$ is methyl or benzyl and the $R^2$ and $R^4$ are either benzyl, phenyl, hydrogen, alkyl with 1 to 4 carbon atoms or hydroxyalkyl with 2 to 4 carbon atoms and $R^3$ is either hydrogen, alkyl with 1 to 4 carbon atoms or hydroxylakyl with 2 to 4 carbon atoms. The compounds of formula I are developer substances which are very favorably tolerated physiologically and enable brilliant hair coloring of great depth of color in the red range.

16 Claims, No Drawings

OXIDATION HAIR DYE COMPOSITION CONTAININNG DIAMINOPYRAZOL DERIVATIVES AND NEW DIAMINOPYRAZOL DERIVATIVES

BACKGROUND OF THE INVENTION

The subject matter of the invention is compositions for the oxidative dyeing of hair based on 3,4- or 4,5-diaminopyrazol derivatives as developer substances and new 3,4- or 4,5-diaminopyrazol derivatives.

In the area of hair coloring, oxidation dyestuffs have achieved considerable importance. The coloring is brought about by means of the reaction of certain developer substances with certain coupler substances in the presence of a suitable oxidizing agent.

In particular, 2,5-diaminotoluene, 2,5-diaminophenylethyl alcohol, p-aminophenol and 1,4-diaminobenzene are used as developer substances. Resorcin, 4-chlororesorcin, 1-naphthol, 3-aminophenol, 5-amino-2-methylphenol and derivatives of m-phenylenediamine are among those coupler substances whose use is preferred.

Numerous special demands are placed on oxidation dyestuffs which are used for dyeing human hair. For example, they must be unobjectionable in toxicological and dermatological respects and must enable the desired intensity of coloring. In addition, a favorable fastness to light, permanent waving, acids and rubbing are required of the achieved hair dyes. But, in every instance, such hair dyes must remain stable over a period of at least 4 to 6 weeks without being influenced by light, rubbing or chemical agents. Moreover, it is necessary that a wide assortment of various color shades can be produced by means of combining suitable developer and coupler substances. In order to achieve natural and especially fashionable shades in the red area, 4-aminophenol is chiefly used, by itself or in a mixture with other developer substances, in combination with suitable coupler substances.

The developer 4-aminophenol, which was chiefly used previously for the red area of the color scale, has recently been criticized for not being physiologically tolerated, while developer substances such as pyrimidine derivatives, which have been recommended more recently, are not completely satisfactory with respect to coloring. The pyrażol derivatives described in DE-OS 2 160 317 such as 3-amino-1-phenyl-2-pyrazolone-5 only dye hair to depths of color which are unusable in hair dyeing practice.

SUMMARY OF THE INVENTION

Therefore, the problem arises of providing an oxidation hair dye composition based on a combination of developer substances and coupler substances containing a developer substance for the red area which is very favorably tolerated physiologically and, together with conventional coupler substances, dyes the hair in brilliant red color shades with a great depth of color.

It has now been found that the proposed problem is solved in an outstanding manner by means of a composition for the oxidative dyeing of hair based on a combination of developer substances and coupler substances containing, as developer substance, a diaminopyrazol of the general formula (I),

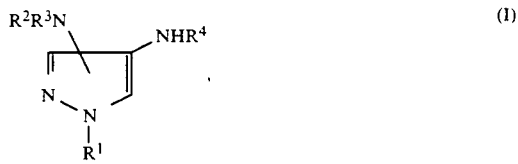

wherein $R^1$, $R^2$ and $R^4$ are identical or different and designate hydrogen, alkyl with 1 to 4 carbon atoms, hydroxyalkyl with 2 to 4 carbon atoms, benzyl or phenyl, and $R^3$ is hydrogen, alkyl with 1 to 4 carbon atoms, hydroxyalkyl with 2 to 4 carbon atoms with the proviso that the amino groups are in 3,4 or 4,5 position, or its physiologically tolerated, water-soluble salt.

The developer substances of formula (I), of which the 3(5),4-diaminopyrazol, 4,5-diamino-1-methylpyrazole and the new 4,5-diamino-I-benzylpyrazol are preferred, are to be contained in the hair dye composition in a quantity of approximately 0.01 to 3.0 percent by weight, preferably 0.1 to 2.5 percent by weight.

Although the advantageous characteristics of the developer substances described here suggest the use of the latter as the only developers, it is also possible, of course, to use the developer substances of formula (I) together with known developer substances such as 1,4-diaminobenzene, 2,5-diaminotoluene or 2,5-diaminophenylethyl alcohol.

Of the known coupler substances, the following are preferably taken into consideration as component part of the hair dye composition described here: resorcin, 4-chlororesorcin, 4,6-dichlororesorcin, 2-methylresorcin, 2-amino-4-(2'-hydroxyethyl)aminoanisole, 2,4-diaminobenzyl alcohol, 2,4-diaminophenylethyl alcohol, m-phenylenediamine, 5-amino-2-methylphenol, 2,4-diaminophenoxyethanol, 4-amino-2-hydroxyphenoxyethanol, 1-naphthol, 3-aminophenol, 3-amino-2-methylphenol, 4-hydroxy-1,2-methylenedioxybenzene, 4-amino-1,2-methylenedioxybenzene, 4-(2'-hydroxyethyl)amino-1,2-methylenedioxybenzene, 2,4-diaminophenetole, 2,4-diamino-5-methylphenetole, 4-hydroxyindole, 3-amino-5-hydroxy-2,6-dimethoxypyridine and 3,5-diamino-2,6-dimethoxypyridine.

The coupler and developer substances can be contained in the hair dye composition individually or in combination with one another.

The total quantity of the combination of developer and coupler substances contained in the hair dye compositions described here is approximately 0.1 to 5.0 percent by weight, wherein a quantity of 0.5 to 4.0 percent by weight is preferred.

The developer components are generally used in approximately equimolar quantities with respect to the coupler components. However, it is not disadvantageous in this respect if the quantity of developer component is present to a certain greater or lesser degree.

Further, the hair dye composition, according to the invention, can contain other coloring components in addition, e.g. 6-amino-2-methylphenol and 2-amino-5-methylphenol, as well as other conventional direct-dyeing dyestuffs, e.g. triphenylmethane dyes, such as Diamond Fuchsine (C.I. 42 510) and Leather Ruby HF (C.I. 42 520), aromatic nitro dyes, such as 2-nitro-1,4-diaminobenzene, 2-amino-4-nitrophenol, 2-amino-5-nitrophenol, 2-amino-4,6-dinitrophenol, 2-amino-5-(2'-hydroxyethyl)aminonitrobenzene and 2-methylamino-5-bis-(2'-hydroxyethyl)aminonitrobenzene, azo dyes such as Acid Brown 4 (C.I. I4 805) and dispersed dyes such as 1,4-diaminoanthraquinone and 1,4,5,8-tetraaminoanthraquinone. The hair dye compositions can contain these dye components in a quantity of approximately 0.1 to 4.0 percent by weight.

Of course, the coupler and developer substances, as well as the other dye components, insofar as they are bases, can also be used in the form of physiologically tolerated salts with organic or inorganic acids, such as hydrochloric acid or sulfuric acid, or—insofar as they have aromatic OH groups—in the form of salts with bases, e.g. as alkali phenolates.

Moreover, other conventional cosmetic ingredients can also be contained in the hair dye composition, e.g. antioxidants such as ascorbic acid, thiogylcolic acid or sodium sulfite, and perfume oils, complexing agents, wetting agents, emulsifying agents, thickeners and hair care materials.

The preparation form of the new hair dye composition can be e.g. a solution, particularly an aqueous or aqueous-alcoholic solution. But the particularly preferred preparation forms are cream, gel or emulsion.

Its composition is a mixture of dyestuff components with the usual ingredients for such preparations.

The usual ingredients in solutions, creams, emulsions or gels are e.g. solvents such as water, lower aliphatic alcohols, e.g. ethanol, propanol and isopropanol, glycerine or glycols such as 1,2-propyleneglycol, wetting agents or emulsifying agents from the classes of anionic, cationic, amphoteric or nonionogenic surface-active substances such as fatty alcohol sulfates, ethoxylated fatty alcohol sulfates, alkyl sulfonates, alkylbenzene sulfonates, alkylbenzene sulfonates, alkyltrimethylammonium salts, alkyl betaines, ethoxylated fatty alcohols, ethoxylated nonylphenols, fatty acid alkanol amides, ethoxylated fatty acid esters, also thickeners such as higher fatty alcohols, starch, cellulose derivatives, vaseline, paraffin oil and fatty acids, as well as hair care materials such as cationic resins, lanolin derivatives, cholesterin, pantothenic acid and betaine. The aforementioned components are used in the amounts which are conventional for such purposes e.g. the wetting agents and emulsifying agents are used in concentrations of approximately 0.5 to 30 percent by weight, the thickeners are used in quantities of approximately 0.1 to 25 percent by weight and the hair care materials are used in a concentration of approximately 0.1 to 5.0 percent by weight.

Depending on the composition, the hair dye composition, according to the invention, can react in a slightly acidic, neutral or alkaline manner. In particular, it has a pH value between 8.0 and 11.5, wherein it is preferably adjusted with ammonia. However, organic amines e.g. monoethanolamine and triethanolamine, or inorganic bases such as sodium hydroxide and potassium hydroxide, can also be used.

For application for the purpose of oxidation dyeing of hair, the aforementioned hair dye composition is mixed immediately prior to use with an oxidizing agent and a quantity of this mixture sufficient for the hair dyeing treatment, generally, approximately 60 to 200 g, depending on the fullness of the hair, is applied to the hair.

Hydrogen peroxide, or its addition compounds in urea, melamine or sodium borate in the form of a 3 to 12 percent, preferably a 6 percent, aqueous solution, chiefly come under consideration as oxidizing agents for the development of the hair coloring. If a 6 percent hydrogen peroxide solution is used as oxidizing agent, then the weight ratio between the hair dye composition and the oxidizing agent is 5:1 to 1:2, but preferably 1:1. Larger quantities of oxidizing agent are used in the hair dye composition chiefly in higher dyestuff concentrations or when a more intensive bleaching of the hair is intended simultaneously. The mixture is allowed to act on the hair at 15° to 50° C. for approximately 10 to 45 minutes, preferably 30 minutes, the hair is then rinsed with water and dried. The hair is washed with a shampoo after this rinse, if necessary, and possibly rerinsed with a weak organic acid such as citric acid or tartaric acid. The hair is then dried.

The production of the developer substances used according to the invention is known in part. Thus, for example, 3(5),4-diaminopyrazol [1] and 4,5-diamino-1-methylpyrazol [2] is described in the literature on the subject: 1) H. Dorn, et al., Liebigs Ann. Chem. 707 (1967), 141–146; 2) H. Dorn, et al., Liebigs Ann. Chem 717 (1968), 118–123. 3,4- and 4,5-diamino-1-methylpyrazol can be produced from the 3(5)-amino-4-nitropyrazol described in text 1) by means of alkylation and subsequent reduction.

The new compounds of the following formulas (II) and (III) and the new 3,4-diamino-1-methylpyrazol can be synthesized in different ways: 3,4-diamino-l-benzylpyrazol can be produced in a manner analogous to the methyl compounds described above by means of benzylation and subsequent reduction. 4,5-diamino-1-benzylpyrazol is produced from the 5-amino-1-benzylpyrazol (H. Dorn, et al., Chem. Ber. 101 (1968), 3265-3277) by means of nitrosation and subsequent reduction.

The derivatives which are alkylated in the amino groups can all be produced, as described in the examples, by means of alkylation of the intermediately formed aminonitropyrazol and subsequent reduction of the nitro groups.

The salts of the compounds of formula (I) are obtainable by means of reaction with organic or inorganic acids or bases.

The developer substances of formula (I) are used in the hair dye composition either as free bases or in the form of their physiologically tolerated salts with inorganic or organic acids, e.g. hydrochloric acid, sulfuric acid, phosphoric acid, acetic acid, propionic acid, lactic acid or citric acid. The compounds of formula (I) are favorably soluble in water. Moreover, they have an excellent shelf stability, particularly as a component of the hair dye composition described here.

The hair dye composition, according to the invention, containing 3,4- or 4,5-diaminopyrazol derivatives as developer substances results in hair colorings with excellent color fastness, particularly with respect to light fastness, washing fastness and rubbing fastness, and the hair dye can be removed again with reducing agents.

The progress achieved in toxicological and dermatological respects by the use of the 3,4- or 4,5-diaminopyrazols in the hair dye composition according to the present application is also of particular significance. The compounds 3(5),4-diaminopyrazol and 4,5-diamino-1-methylpyrazol are not mutagenic.

With respect to dyeing characteristics, the hair dye composition, according to the invention, offers possibilities reaching far beyond the substitution of conventionally used 4-aminophenols. Brilliant red shades with extraordinary depth of color can be produced, which can not be achieved with conventional current color components. But in addition to this application in the highly fashionable area, natural color shades can also be produced by means of use in combination with suitable coupler components without requiring an additional developer component of the p-phenylenediamine type.

The very good dyeing properties of the hair dye composition, according to the present application, can also be seen in that this composition enables gray hair, which is not chemically damaged beforehand, to be dyed easily and with good covering power. The subject matter of the present patent application is, in addition, new diaminopyrazol derivatives such as 3,4-diamino-1-methylpyrazol and diaminopyrazol derivatives of the general formula (II)

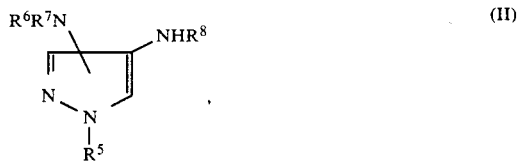

(II)

wherein $R^5$ is a benzyl group, $R^6$ and $R^8$ are identical or different and designate hydrogen, alkyl with 1 to 4 carbon atoms, hydroxyalkyl with 2 to 4 carbon atoms, benzyl or phenyl, and $R^7$ is hydrogen, alkyl with 1 to 4 carbon atoms or hydroxyalkyl with 2 to 4 carbon atoms, with the proviso that the amino groups are in 3,4 or 4,5 position, wherein 4,5-diamino-1-benzylpyrazol, 3,4-diamino-I-benzylpyrazol, 4-amino-1-benzyl-3-(2'-hydroxyethyl)aminopyrazol and 4-amino-1-benzyl-3-benzylaminopyrazol are mentioned in particular, as well as further diaminopyrazol derivatives of the general formula (III)

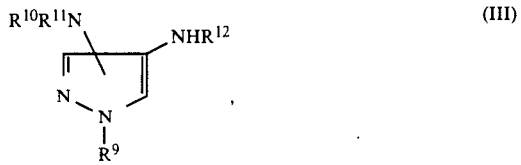

(III)

wherein $R^9$ is a methyl group, $R^{10}$ and $R^{12}$ are identical or different and designate hydrogen, alkyl with 1 to 4 carbon atoms, hydroxyalkyl with 2 to 4 carbon atoms, benzyl or phenyl, and $R^{11}$ is hydrogen, alkyl with 1 to 4 carbon atoms, hydroxyalkyl with 2 to 4 carbon atoms, with the proviso that the amino groups are in 3,4 or 4,5 position, and at least one of the groups $R^{10}$ to $R^{12}$ is different than hydrogen, wherein 4-amino-1-methyl-3-methylaminopyrazol and 4-amino-l-methyl-5-N,N-dimethylaminopyrazol are mentioned in particular.

The subject matter of the invention is explained in more detail in the following examples without being limited to these examples.

While the invention has been illustrated and described as embodied in oxidation hair dye compositions containing diaminopyrazol derivatives and new diaminopyrazol derivatives, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

Production Examples

EXAMPLE 1

Synthesis of 3,4-diamino-1-benzylpyrazol

Step 1: Reaction of 3(5)-amino-4-nitropyrazol with benzylbromide 1.00 g (7.80 mmoles) of 3(5)-amino-4-nitropyrazol are mixed in 30 ml absolute dioxane with 187 mg (7.80 mmoles) of sodium hydride. After the hydrogen development is concluded, 1.33 g (7.80 mmoles) of benzylbromide are added to the reaction mixture by drops and the mixture is heated to boiling for 17 hours. The solvent is then distilled off in the rotary evaporator in vacuum and the residue is separated by means of column chromatography using silica gel with a mixture of toluene and either (8:1).

1st Fraction

A brown oil is obtained which was distilled in a bulb tube at 200° C./0.05 torr and crystallized after processing with a mixture of chloroform and carbon tetrachloride.

Yield 430 mg (17.9 percent of theoretical) of 1-benzyl-3-benzylamino-4-nitropyrazol as lustrous yellow crystals with a melting point of 76° C. (chloroform/carbon tetrachloride).

| 60-MHz-$^1$H-NMR (CDCl$_3$): | |
|---|---|
| $\delta =$ 7.71 | (s; 1 H) |
| 7.28 | (s; 10 H) |
| 6.12 | (s; 1 H; exchangeable with D$_2$O) |
| 5.03 | (s; 2 H) |
| 4.55–4.48 ppm | (d; 2 H; J = 6 Hz; —NH—CH$_2$—) |

For this and all following NMR spectra: s=singlet, d=doublet, t=triplet, m=multiplet MS (70 eV): m/e (percent)=(308; M+), 290 (15), 105 (24) 91 (100), 55 (24).

For this and all following mass spectra: The relative intensity of the molecular fragments is indicated in percent, wherein the molecular fragment with the greatest intensity is equal to 100 percent.

UV (CH$_2$Cl$_2$):$\lambda_{max}$ (log $\epsilon$)=281 (3.90), 373 nm (4.07).

C$_{17}$H$_{16}$N$_4$O$_2$ (308.34)

Calculated: C 66.22, H 5.23, N 18.17.
Found: C 66.40, H 5.31, N 18.18.

2nd Fraction 1.33 g (78.1 percent of theoretical) of 3-amino-1-benzyl-4-nitropyrazol as yellow needles with a melting point of 140° C. (ether).

60-MHz-¹H-NMR (D₆-DMSO):
δ =  8.59   (s; 1 H)
     7.28   (s; 5 H)
     6.18   (s; 2 H; exchangeable with D₂O)
     5.09 ppm   (s; 2 H)
MS (70 eV): m/e (percent) = 218 (82, M+), 201 (6), 91 (100), 65 (35).
UV (CH₂Cl₂): $\lambda_{max}$ (log ε) = 278 (3.89), 343 nm (3.72).
$C_{10}H_{10}N_4O_2$ (218.20)

Calculated: C 55.05, H 4.62, N 25.68.
Found: C 54.80, H 4.47, N 25.73.

Step 2

Reduction of 3-amino-1-benzyl-4-nitropyrazol 1.00 g (4.58 mmoles) of 1-benzyl-3-amino-4-nitropyrazol are hydrated in 100 ml absolute methanol with catalytic quantities of palladium/carbon (10 percent) at room temperature and 50 bar. After 17 hours, the hydration is concluded and hydrogen chloride gas is guided through the filtrated solution for 5 minutes. The solution is reduced in the rotary evaporator in a vacuum to ⅓ of the original volume and then mixed with acetic acid until a precipitate is formed which is subsequently recrystallized from acetic acid/methanol.

Yield 980 mg (76.6 percent of theoretical) of 3,4-diamino-1-benzylpyrazol dihydrochloride hydrate as pale pink crystals with a melting point of 139° C. (acetic acid/methanol).

60-MHz-¹H-NMR (D₆-DMSO):
δ =  7.51   (s; 1 H)
     7.25   (s; 5 H)
     6.82   (s; 8 H; exchangeable with D₂O)
     5.24 ppm   (s; 2 H)
$C_{10}H_{14}Cl_2N_4 * H_2O$ Calculated: C 43.02, H 5.77, N 20.06.
Found: C 43.26, H 5.64, N 20.23.

EXAMPLE 2

Synthesis of 4-amino-1-benzyl-3-benzylaminopyrazol dihydrochloride 500 mg (1.62 mmoles) of 1-benzyl-3-benzylamino-4-nitropyrazol (Example 1, Step I, Fraction 1) are hydrated in 20 ml 5-normal methanolic hydrochloric acid with catalytic quantities of palladium/carbon at room temperature and 50 bar. After 17 hours, the hydration is concluded and hydrogen chloride gas is guided through the solution for 5 minutes. The solution is reduced in the rotary evaporator in a vacuum to half of the original volume and then mixed with acetic acid until a colorless precipitate is formed which is recrystallized from acetic acid/methanol.

Yield 350 mg (61.5 percent of theoretical) of 4-amino-1-benzyl-3-benzylaminopyrazol dihydrochloride as colorless crystals with a melting point of 149° C. (acetic acid/methanol).

60-MHz-¹H-NMR (D₆-DMSO):
δ =  9.10   (s; 5 H; exchangeable with D₂O)
     7.89   (s; 1 H)
     7.18   (s; 10 H)
     5.10   (s; 2 H)
     4.35 ppm   (s; 2 H)
$C_{17}H_{20}Cl_2N_4$ (351.28)

Calculated: C 58.13, H 5.74, N 15.95.
Found: C 57.82, H 5.74, N 16.19.

EXAMPLE 3

Synthesis of 4-amino-3-(2'-hydroxyethyl)amino-1-benzylpyrazol

Step 1

Synthesis of N-3-(1-benzyl-4-nitropyrazolyl) carbamic acid-β-bromoethyl ester 2.00 g (9.17 mmoles) of 3-amino-1-benzyl-4-nitropyrazol are mixed in 30 ml absolute tetrahydrofuran with 1.54 g (15.4 mmoles) of calcium carbonate and heated to 60° Celsius. 2.40 g (12.8 mmoles) of chloroformic acid-β-bromoethyl ester are added by drops to the solution and the reaction mixture is heated to boiling for 6 hours. The reaction mixture is filtrated and the filtrate is then evaporated to half its volume in the rotary evaporator. Pale yellow crystals are obtained which are recrystallized from ether.

Yield 2.31 g (68.2 percent of theoretical) of N-3-(1-benzyl-4-nitropyrazolyl) carbamic acid-β-bromoethyl ester as pale yellow crystals with a melting point of 102° C. (ether).

60-MHz-¹H-NMR (D₆-DMSO):
δ =  9.80   (s; 1 H; exchangeable with D₂O)
     8.90   (s; 1 H)
     7.32   (s; 5 H)
     5.30   (s; 2 H)
     4.50–4.21   (t; 2 H)
     3.77–3.50 ppm   (t; 2 H)
MS (70 eV): m/e (percent) = 370 (6, M+, ⁸¹Br), 368 (6; M+; ⁷⁹Br), 324 (3; ⁸¹Br), 322 (3; ⁷⁹Br), 231 (3), 91 (100), 65 (23).
UV (CH₂Cl₂): $\lambda_{max}$ (log ε) = 279 (3.86), 314 nm sh (3.81).
$C_{13}H_{13}BrN_4O_4$ (369.20)

Calculated: C 42.29, H 3.55, N 15.18.
Found: C 42.23, H 3.28, N 15.22.

Step 2

Synthesis of N-(1-benzyl-4-nitropyrazolyl)-oxazolidine-2-one 400 mg (1.10 mmoles) of N-3-(1-benzyl-4-nitropyrazolyl) carbamic acid-β-bromoethyl ester are stirred in 10 ml 4 normal sodium hydroxide solution for 17 hours at room temperature. The obtained precipitate is recrystallized from acetic acid.

Yield 260 mg (82.0 percent of theoretical) of N-(1-benzyl-4-nitropyrazolyl)oxazolidine-2-one as bright yellow crystals with a melting point of 120° C. (acetic ester).

60-MHz-¹H-NMR (CDCl₃):
δ =  7.98   (s; 1 H)
     7.29   (s; 5 H)
     5.18   (s; 2 H)

-continued

| | |
|---|---|
| 4.66–4.32 | (t; 2 H) |
| 4.15–3.85 ppm | (t; 2 H) |
| UV (CH$_2$Cl$_2$): $\lambda_{max}$ (log $\epsilon$) = 271 nm (3.85). | |
| C$_{13}$H$_{12}$N$_4$O$_4$ (288.30) | |

Calculated: C 54.16, H 4.20, N 19.43.
Found: C 53.96, H 4.17, N 19.55.

Step 3

Synthesis of
1-benzyl-3-($\beta$-hydroxyethyl)amino-4nitropyrazol 1 00 g (0.35 mmoles) of N-(1-benzyl-4-nitropyrazolyl) oxazolidine-2-one is heated in 10 ml 5 normal sodium hydroxide solution for 4 hours at 70° C. The solvent is distilled off in the rotary evaporator in vacuum and the residue is separated by means of column chromatography using silica gel with a mixture of chloroform and methanol (10:1).

1st Fraction 14 mg (13.9 percent of theoretical) of N-(1-benzyl-4-nitropyrazolyl)oxazolidine-2-one with a melting point of 120° C. (acetic ester).

2nd Fraction 72 mg (78.4 percent of theoretical) of 1-benzyl-3-($\beta$-hydroxyethyl)amino-4-nitropyrazol as lustrous yellow crystals with a melting point of 94° C.

| 60-MHz-$^1$H-NMR (CDCl$_3$): | |
|---|---|
| $\delta$ = 7.70 | (s; 1 H) |
| 7.32 | (s; 5 H) |
| 6.10 ppm | (s; 1 H; exchangeable with D$_2$O) |
| 5.05 | (s; 2 H) |
| 3.98–3.32 | (m; 4 H) |
| 2.89–2.60 ppm | (t; 1 H; exchangeable with D$_2$O). |
| MS (70 eV): m/e (percent) = | 262 (13; M+), 231 (63), 218 (13), 91 (100), 65 (22). |
| UV (CH$_2$Cl$_2$): $\lambda_{max}$ (log $\epsilon$) = | 279 (3.89), 370 nm (3.75). |
| C$_{12}$H$_{14}$N$_4$O$_3$ (262.39) | |

Calculated: C 54.95, H 5.38, N 21.36.
Found: C 54.87, H 5.48, N 21.45.

Step 4

Reduction of
1-benzyl-3-(2'-hydroxyethyl)amino-4-nitropyrazol 250 mg (0.76 mmoles) of 1-benzyl-3-(2'-hydroxyethyl)amino-4-nitropyrazol are mixed with 4 ml of a 4.4 percent solution of formic acid in methanol and catalytic quantities of palladium/carbon (10 percent). It is stirred for 48 hours at room temperature in a nitrogen atmosphere, the catalyst is filtrated off and the solvent is distilled off in the rotary evaporator in vacuum. The residue is dried in vacuum. The yield is quantitative.

| 60-MHz-$^1$H-NMR (CDCl$_3$): | |
|---|---|
| $\delta$ = 8.02 | (s; 4 H; exchangeable with D$_2$O) |
| 7.20 | (s; 6 H) |
| 5.00 | (s; 2 H) |
| 3.90–3.15 ppm | (m; 4 H) |

EXAMPLE 4

Synthesis of 4,5-diamino-1-methylpyrazolium hydrogen sulfate hydrate

Step 1

Synthesis of 3- and 5-amino-1-methyl-4-nitropyrazol 4.00 g (31.7 mmoles) of dimethyl sulfate are added slowly by drops to 2.00 g (15.6 mmoles) of 3(5)-amino-4-nitropyrazol in 50 ml of 2 normal sodium hydroxide solution accompanied by stirring. It is stirred for 17 hours at room temperature. The resulting precipitate is removed by suction and washed with methanol.

Yield 1.54 g (69.5 percent of theoretical) of 3- and 5-amino-1-methyl-4-nitropyrazol as substance mixture. The chromatographic separation of the substance mixture using a silica gel column (1=100 cm; d=3 cm) with chloroform/methanol 10:1 as running agent gives:

1st Fraction 680 mg (45.3 percent of theoretical) of 3-amino-1-methyl-4-nitropyrazol (Rf-value 0.53 CHCl$_3$/CH$_3$OH 10:1 ) with a melting point of 194° C.

2nd Fraction 380 mg (24.7 percent of theoretical) of 5-amino-1-methyl-4-nitropyrazol (Rf-value 0.37 CHCl$_3$/CH$_3$OH 10:1) with a melting point of 266° C.

Step 2

Synthesis of 4,5-diamino-1-methylpyrazolium hydrogen sulfate hydrate 200 mg (1.41 mmoles) of 4-amino-1-methyl-5-nitropyrazol are hydrated in 50 ml absolute methanol with catalytic quantities of palladium/carbon at room temperature and 30 bar. The hydration is terminated at 17 hours. A colorless precipitate is precipitated out of the filtrated solution when adding 135 mg (1.41 mmoles) of concentrated sulfuric acid, which precipitate is removed by suction and recrystallized from water.

Yield 150 mg (46.6 percent of theoretical) of 4,5-diamino-1-methylpyrazolium hydrogen sulfate hydrate as colorless crystals with a melting point of 200–201° C. (decomposition) (water).

| 60-MHz-$^1$H-NMR (D$_6$-DMSO): | |
|---|---|
| $\delta$ = 7.25 | (s; 1 H) |
| 7.18–6.20 | (s; 8 H; exchangeable with D$_2$O) |
| 3.61 ppm | (s; 3 H) |
| C$_4$H$_{12}$N$_4$O$_5$S (228.23) | |

Calculated: C 21.05, H 5.30, N 24.55.
Found: C 20.86, H 5.35, N 24.29.

EXAMPLE 5

Synthesis of 3,4-diamino-1-methylpyrazol 90 mg (0.63 mmoles) of 3-amino-1-methyl-4-nitropyrazol are hydrated in 80 ml absolute methanol with catalytic quantities of palladium/carbon at room temperature and 50 bar. After the solvent is reduced to ⅓ the original volume in the rotary evaporator in vacuum, a white precipitate is recipitated out of the filtrated solution when adding 124 mg (1.26 mmoles) of concentrated sulfuric acid, the precipitate is removed by suction and dried. The hydration is concluded after 17 hours.

Yield:

100 mg (75.5 percent of theoretical) of 3,4-diamino-1-methylpyrazolium hydrogen sulfate as white crystals with a melting point of 214–215° C. (methanol).

300-MHz-$^1$H-NMR (D$_6$-DMSO):
δ = 7.55 (s; 1 H)
7.67–7.20 (m; 6 H; exchangeable with D$_2$O)
3.60 ppm (s; 3 H)
C$_4$H$_8$N$_4$* 1,1 H$_2$SO$_4$ (220.01)

Calculated: C 21.84, H 4.67, H 25.46.
Found: C 21.83, H 4.63, N 25.18.

Example 6

Synthesis of 4-amino-1-methyl-3-methylaminopyrazolium hydrogen sulfate

Step 1

Synthesis of 3-trifluoroacetylamino-1-methyl-4-nitropyrazol

Method A 7.50 ml trifluoroacetic anhydride are mixed by portions with 1.50 g (I0.6 mmoles) of 3-amino-I-methyl-4-nitropyrazol. The solvent is distilled off in the rotary evaporator in vacuum after stirring for 17 hours at room temperature and the residue is mixed with hexane/ether, wherein a white precipitate crystallizes out.

Yield 2.40 (95.4 percent of theoretical) of 3-trifluoroacetylamino-1-methyl-4-nitropyrazol as white needles with a melting point of 104° C. (ether).

60-MHz-$^1$H-NMR (CDCl$_3$):
δ = 9.72 (s; 1 H; exchangeable with D$_2$O)
8.12 (s; 1 H)
3.98 ppm (s; 3 H).
MS (70 eV): m/e (percent) = 238 (81; M+), 169 (100), 152 (63), 125 (13), 69 (31), 52 (37), 42 (66).
UV (CH$_2$Cl$_2$): λ$_{max}$ (log ε) = 292 nm (3.89).
C$_6$H$_5$F$_3$N$_4$O$_3$ (238.12)

Calculated: C 30.26, H 2.11, N 23.53.
Found: C 30.21, H 1.94, N 23.5.

Method B 5.00 ml concentrated sulfuric acid are mixed by portions with 1.00 g (5.2I mmoles) of 3-trifluoroacetylamino-1-methylpyrazol. 1 ml 100 percent nitrating acid is then added by drops and it is stirred for 17 hours at room temperature. The solution is poured on 40 g ice, wherein a colorless precipitate crystallizes out, which precipitate is removed by suction and dried.

Yield 270 mg (22.2 percent of theoretical) of 3-trifluoroacetylamino-1-methyl-4-nitropyrazol with a melting point of 104° C. (ether).

The mother liquor is neutralized with concentrated ammonia and extracted for 24 hours with ether in a rotary perforator. When the organic phase is reduced, another 220 mg (18.1 percent of theoretical) of 3-trifluoroacetylamino-1-methyl-4-nitropyrazol are isolated.

Step 2

Synthesis of 1-methyl-3-methylamino-4-nitropyrazol 100 g (4.20 mmoles) of 3-trifluoroacetylamino-1-methyl-4-nitropyrazol are heated with 2.12 g (16.8 mmoles) methyl iodide in 10 ml absolute acetone to 50° C. 940 mg (16.8 mmoles) powdered potassium hydroxide are then added and the reaction mixture is heated to boiling for 5 minutes. The solvent is distilled off in the rotary evaporator in vacuum and the residue is separated by means of column chromatography using silica gel with ether/toluene (5:1).

1st Fraction 370 mg (62.0 percent of theoretical) of 1-methyl-3-methylamino-4-nitropyrazol as lustrous yellow crystals with a melting point of 176° C. (ether).

60-MHz-$^1$H-NMR (D$_6$-DMSO):
δ = 8.38 (s; 1 H)
6.40 (s; 1 H; exchangeable with D$_2$O)
3.68 (s; 3 H; methyl group on pyrazol ring)
2.82–2.72 ppm (d; 3 H; J = 6 Hz; —NH—CH$_3$).
MS (70 eV): m/e (percent) = 156 (53; M+), 138 (15), 109 (24), 71 (53), 68 (56), 52 (44), 42 (100).
UV (CH$_2$Cl$_2$): λ$_{max}$ (log ε) = 280 (3.85), 373 nm (3.75).
C$_5$H$_8$N$_4$O$_2$ (156.14)

Calculated: C 38.46, H 5.16, N 35.88.
Found: C 38.21, H 5.22, N 35.75.

210 mg (35.2 percent of theoretical) of 3-amino-1-methyl-4-nitropyrazol were isolated as 2nd fraction.

Step 3

Synthesis of 4-amino-1-methyl-3-methylaminopyrazolium hydrogen sulfate 500 mg (3.20 mmoles) of 1-methyl-3-methylamino-4-nitropyrazol are hydrated in 50 ml absolute methanol with catalytic quantities of palladium/carbon at room temperature and 30 bar. The hydration is concluded after 17 hours, a pale orange precipitate is precipitated out of the filtrated solution when adding 314 mg (3.20 mmoles) of concentrated sulfuric acid, which precipitate is removed by suction and dried.

Yield 590 mg (82.2 percent of theoretical) of 4-amino-1-methyl-3-methylaminopyrazolium hydrogen sulfate as pale orange crystals with a melting point of 209° C.

60-MHz-$^1$H-NMR (D$_6$-DMSO):
δ = 8.07 (s; 5 H; exchangeable with D$_2$O)
7.52 (s; 1 H)
3.58 (s; 3 H; methyl group on pyrazol ring)
C$_5$H$_{12}$N$_4$O$_4$S (224.24)

Calculated: C 26.78, H 5.39, N 24.99.
Found: C 26.42, H 5.38, N 24.91.

EXAMPLE 7

Synthesis of 4-amino-5-(N,N-dimethylamino)-1-methylpyrazolium dihydrosulfate

Step 1

Reaction of a mixture of 3- and 5-trifluoroacetylamino-1-methyl-4-nitropyrazol with methyl iodide 3.94 g (16 5 mmoles) of a mixture of 3- and 5-trifluoroacetylamino-1-methyl-4-nitropyrazol are heated with 8.48 g (16.8 mmoles) methyl iodide in 40 ml absolute acetone to 50° C. 3.77 mg (16.8 mmoles) powdered potassium hydroxide are then added and the solution is heated to boiling for 5 minutes. The solvent is distilled off in the rotary evaporator in vacuum and the residue is separated by means of column chromatography using silica gel with ether/toluene (5:1).

1st Fraction 980 mg (34.8 percent of theoretical) of 5-(N,N-dimethylamino)-1-methyl-4-nitropyrazol as yellow oil which is distilled in a bulb tube at 50° C./0.04 torr.

60-MHz-$^1$H-NMR (CDCl$_3$):
$\delta =$ 7.95 (s; 1 H)
3.72 (s; 3 H)
2.89 ppm (s; 6 H)
MS (70 eV): m/e (percent) = 170 (22; M+), 153 (31), 146 (21), 125 (90), 123 (62), 108 (55), 82 (70), 70 (99), 66 (92), 42 (100).

$C_6H_{10}N_4O_2$ (170.17)

Calculated: C 42.35, H 5 92, N 32.92.
Found: C 42.14, H 5.99, N 35.75.

2nd Fraction 1.38 mg (53.4 percent of theoretical) of 1-methyl-3-methylamino-4-nitropyrazol as lustrous yellow crystals with a melting point of 176° C. (ether).

Step 2

Synthesis of 4-amino-5-(N,N-dimethylamino)-1-methylpyrazolium dihydrosulfate 560 mg (3.29 mmoles) of 5-(N,N-dimethylamino)-1-methyl-4-nitropyrazol are hydrated in 75 ml absolute methanol with catalytic quantities of palladium/carbon at room temperature and 30 bar. The hydration is concluded after 17 hours. 645 mg (6.58 mmoles) of concentrated sulfuric acid are added and the catalyst is filtrated off. The solvent is distilled off and the residue is mixed with 2-propanol, wherein a colorless precipitate is crystallized out.

Yield 300 mg (27.1 percent of theoretical) of 4-amino-5-(N,N-dimethylamino)-1-methylpyrazolium dihydrosulfate with a melting point of 139° C. (2-propanol).

60-MHz-$^1$H-NMR (D$_6$-DMSO):
$\delta =$ 9.78 (s; 6 H; exchangeable with D$_2$O)
7.35 (s; 1 H)
3.61 (s; 3 H)
2.78 ppm (s; 6 H)

$C_6H_{16}N_4O_8S_2$ (336.35)

Calculated: C 21.42, H 4.79, N 16.66.
Found: C 21.11, H 4.72, N 16.37.

EXAMPLES FOR HAIR DYE COMPOSITION

EXAMPLE 8

Hair dye composition in gel form

| | |
|---|---|
| 0.50 g | 3,4-diaminopyrazol dihydrochloride |
| 0.50 g | 5-amino-2-methylphenol |
| 0.15 g | sodium sulfite, anhydrous |
| 5.00 g | lauryl alcohol diglycol ether sulfate sodium salt (28 percent aqueous solution) |
| 1.00 g | hydroxyethyl cellulose (highly viscous) |
| 10.00 g | ammonia (22 percent aqueous solution) |
| 82.85 g | water |
| 100.00 g | |

50 g of the hair dye composition described above are mixed with 50 g hydrogen peroxide solution (6 percent) shortly before use, and the mixture is then applied to blond natural hair. After letting it act for a period of 30 minutes at 40° C., the hair is rinsed with water and dried. The hair has an intensive, lustrous red-orange coloring.

EXAMPLE 9

Hair dye composition in gel form

| | |
|---|---|
| 0.35 g | 4,5-diamino-1-methylpyrazol dihydrochloride |
| 0.27 g | 3-aminophenol |
| 0.30 g | ascorbic acid |
| 15.00 g | oleic acid |
| 7.00 g | isopropanol |
| 10.00 g | ammonia (22 percent aqueous solution) |
| 67.08 g | water |
| 100.00 g | |

Shortly before use, 50 g of this hair dye composition are mixed with 50 g hydrogen peroxide solution (6 percent) and the mixture is allowed to act on white human hair for 30 minutes at 40° C. It is then rinsed with water and dried. The hair is dyed a lustrous red shade.

EXAMPLE 10

Hair dye composition in cream form

| | |
|---|---|
| 1.00 g | 4-amino-5-(N,N-dimethylamino)-1-methylpyrazolium dihydrosulfate according to Example 7 |
| 1.10 g | 1-naphthol |
| 15.00 g | cetyl alcohol |
| 0.30 g | sodium sulfite, anhydrous |
| 3.50 g | lauryl alcohol diglycol ether sulfate sodium salt (28 percent aqueous solution) |
| 3.00 g | ammonia (22 percent aqueous solution) |
| 76.10 g | water |
| 100.00 g | |

50 g of this hair dye composition are mixed with 50 g hydrogen peroxide solution (6 percent) shortly before using. The mixture is then applied to natural blond hair and allowed to act for 30 minutes at 40° C. The hair is then rinsed with water and dried. The hair has obtained an intensive salmon-red coloring.

EXAMPLE 11

Hair dye solution

| | |
|---|---|
| 0.50 g | 3,4-diaminopyrazol dihydrochloride |
| 0.50 g | 2-amino-5-methylphenol |
| 0.50 g | 2-amino-4-(2'-hydroxyethyl)amino anisole sulfate |
| 0.05 g | 1-naphthol |
| 10.00 g | lauryl alcohol diglycol ether sulfate sodium salt (28 percent aqueous solution) |
| 10.00 g | ammonia (22 percent aqueous solution) |
| 78.45 g | water |
| 100.00 g | |

50 g of the hair dye composition described above are mixed with 50 g hydrogen peroxide solution (6 percent) shortly before use, and the mixture is allowed to act for 30 minutes at 40° C. on blond natural hair. The hair is then rinsed with water and dried. The hair is colored a fashionable dark brown rosewood shade.

EXAMPLE 12

Dye composition in gel form

| | |
|---|---|
| 1.00 g | 4,5-diamino-1-methylpyrazol dihydrochloride |
| 2.00 g | 2,5-diaminotoluene sulfate |
| 1.50 g | 2-amino-4-(2'-hydroxyethyl)amino anisole sulfate |
| 0.10 g | 1-(2'-ureidoethyl)amino-4-nitrobenzene |
| 0.15 g | sodium sulfite, anhydrous |
| 2.50 g | lauryl alcohol diglycol ether sulfate sodium salt (28 percent aqueous solution) |
| 0.80 g | hydroxyethyl cellulose, highly viscous |
| 6.00 g | ammonia, (22 percent aqueous solution) |
| 88.95 g | water |
| 100.00 g | |

50 g of the hair dye composition described above are mixed with 50 g hydrogen peroxide solution (6 percent) shortly before use and the mixture is then applied to blond natural hair. After allowing it to act for a period of 30 minutes at 40° C., the hair is rinsed with water and dried. The hair has obtained a black coloring.

EXAMPLES 13 to 27

Hair dye solutions

The solution according to Example 8 is used and the 3,4-diaminopyrazol dihydrochloride is replaced in identical quantities with other pyrazol derivatives ("developers") of formula (I) from Examples 1–7 and the 5-amino-2-methylphenol is replaced in identical quantities with the "couplers" indicated in Table 1

TABLE 1

| Example | Developer of formula (I) from Example | Coupler | Color |
|---|---|---|---|
| 13 | 1 | 5-amino-2-methylphenol | lustrous red-orange |
| 14 | 2 | 5-amino-2-methylphenol | red |
| 15 | 3 | 5-amino-2-methylphenol | orange |
| 16 | 6 | 5-amino-2-methylphenol | orange |
| 17 | 7 | 5-amino-2-methylphenol | brick-red |
| 18 | 1 | 3-aminophenol | lustrous red |
| 19 | 3 | 3-aminophenol | red |
| 20 | 6 | 3-aminophenol | red |
| 21 | 7 | 3-aminophenol | red |
| 22 | 1 | 2-amino-4-(2'-hydroxyethyl)amino-anisol sulfate | violet |
| 23 | 2 | 2-amino-4-(2'-hydroxyethyl)amino-anisole sulfate | gray-blue |
| 24 | 3 | 2-amino-4-(2'-hydroxyethyl)amino-anisole sulfate | gray-violet |
| 25 | 5 | 2-amino-4-(2'-hydroxyethyl)amino-anisole sulfate | gray-violet |
| 26 | 6 | 2-amino-4-(2'-hydroxyethyl)amino-anisole sulfate | violet |
| 27 | 7 | 2-amino-4-(2'-hydroxyethyl)amino-anisole sulfate | blue-violet |

All of the percentages given in the present patent application are percent by weight unless otherwise indicated.

What is claimed is:

1. Composition for oxidative dyeing of hair based on a combination of developer substances and coupler substances, containing as a developer substance, a member selected from the group consisting of diaminopyrazoles of the general formula (I),

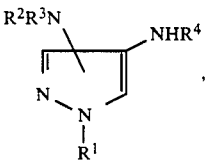

wherein $R^1$, $R^2$ and $R^4$ are each independently selected from the group consisting of hydrogen, alkyl with 1 to 4 carbon atoms, hydroxyalkyl with 2 to 4 carbon atoms, benzyl and phenyl, and $R^3$ is selected from the group consisting of hydrogen, alkyl with 1 to 4 carbon atoms and hydroxyalkyl with 2 to 4 carbon atoms, with the proviso that the $R^2R^3N$ and $NHR^4$ groups are in a 3 and 4 or 4 and 5 positions of said diaminopyrazol, and water-soluble salts thereof.

2. Composition according to claim 1, wherein the diaminopyrazol is selected from the group consisting of 3,4-diaminopyrazol, 4,5-diaminopyrazol, 4,5-diamino-1-methylpyrazol and 4,5-diamino-1-benzylpyrazol.

3. Composition according to claim 1, wherein the developer substance of formula (I) is contained in a quantity of 0.01 to 3.0 percent by weight.

4. Composition according to claim 1, wherein the coupler substance is selected from the group consisting of 1-naphthol, resorcin, 4-chloro-resorcin, 4,6-dichlororesorcin, 2-methylresorcin, 2-amino-4-(2'-hydroxyethyl)aminoanisole, 5-amino-2-methylphenol, 2,4-diaminophenoxyethanol, 4-amino-2-hydroxyphenoxyethanol, 3-aminophenol, 3-amino-2-methylphenol, 4-hydroxy-1,2-methylenedioxybenzene, 4-amino-1,2-methylenedioxybenzene, 4-(2'-hydroxyethyl)amino-1,2-methylenedioxybenzene, 2,4-diaminophenetole, 2,4-diamino-5-methylphenetole, 2,4- diaminobenzyl alcohol, m-phenylenediamine, 2,3-diaminophenylethyl alcohol, 4-hydroxyindole, 3-amino-5-hydroxy-2,6-dimethoxypyridine and 3,5-diamino-2,6-dimethoxypyridine.

5. Compositions according to claim 1, wherein the total quantity of the combination of developer and coupler substances is 0.1 to 5.0 percent by weight.

6. Composition according to claim 1, further comprising a dye component selected from the group consisting of 6-amino-2-methylphenol, 2-amino-5-methylphenol, Diamond Fuchsine (C.I. 42 510), Leather Ruby HF (C.I. 42 520), 2-nitro-1,4-diaminobenzene, 2-amino-4-nitrophenol, 2-amino-5-nitrophenol, 2-amino-4,6-dinitrophenol, 2-amino-5-(2'-hydroxyethyl)aminonitrobenzene, 2-methylamino-5-bis-(2'-hydroxyethyl)aminonitrobenzene, Acid Brown 4 (C.I. 14 805), 1,4-diaminoanthraquinone and 1,4,5,8-tetraaminoanthraquinone.

7. Composition according to claim 1, wherein said diaminopyrazol is 3,4-diamino-1-methylpyrazol.

8. Diaminopyrazol derivative of the general formula (II)

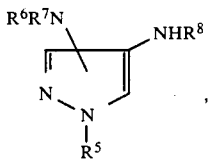

wherein $R^5$ is a benzyl group, $R^6$ and $R^8$ are each independently selected form the group consisting of hydrogen, alkyl with 1 to 4 carbon atoms, hydroxyalkyl with 2 to 4 carbon atoms, benzyl and phenyl, and $R^7$ is selected from the group consisting of hydrogen, alkyl with 1 to 4 carbon atoms and hydroxyalkyl with 2 to 4 carbon atoms, with the proviso that the $R^6R^7N$ and $NHR^8$ groups are in the 3 and 4 or 4 and 5 positions of said diaminopyrazol.

9. Diaminopyrazol derivative according to claim 8, comprising 4,5-diamino-1-benzylpyrazol.

10. Diaminopyrazol derivative according to claim 8, comprising 3,4-diamino-1-benzylpyrazol.

11. Diaminopyrazol derivative according to claim 8, comprising 4-amino-1-benzyl-3-(2'-hydroxyethyl)aminopyrazol.

12. Diaminopyrazol derivative according to claim 8, comprising 4-amino-1-benzyl-3-benzylaminopyrazol.

13. Diaminopyrazol derivative of the general formula (III)

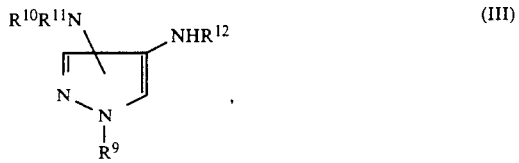

wherein $R^9$ is a methyl group, $R^{10}$ and $R^{12}$ are each independently selected from the group consisting of hydrogen, alkyl with 1 to 4 carbon atoms, hydroxyalkyl with 2 to 4 carbon atoms, benzyl and phenyl, and $R^{11}$ is selected from the group consisting of hydrogen, alkyl with 1 to 4 carbon atoms and hydroxyalkyl with 2 to 4 carbon atoms, with the proviso that the $R^6R^7N$ and $NHR^8$ groups are in the 3 and 4 or 4 and 5 positions of said diaminopyrazol, and at least one of the groups $R^{10}$ to $R^{12}$ is different than hydrogen.

14. Diaminopyrazol derivative according to claim 13, comprising 4-amino-1-methyl-3-methylaminopyrazol.

15. Diaminopyrazol derivative according to claim 13, comprising 4-amino-1-methyl-5-N,N-dimethylaminopyrazol.

16. Composition according to claim 5, wherein said total quantity of developer and coupler substances is from 0.5 to 4.0 percent by weight.

* * * * *

UNITED STATES PATENT AND TRADEMARK OFFICE
CERTIFICATE OF CORRECTION

PATENT NO. : 5,061,289
DATED : October 29, 1991
INVENTOR(S) : Thomas Clausen, et al It is certified that error appears in the above-identified patent and that said Letters Patent is hereby corrected as shown below:

Col. 18, lines 26 to 27, please delete

"$R^6R^7N$ and $NHR^8$" and and change it to:

--$R^{10}R^{11}N$ and $NHR^{12}$--

Signed and Sealed this

Eighth Day of June, 1993

Attest:

MICHAEL K. KIRK

Attesting Officer     Acting Commissioner of Patents and Trademarks